United States Patent
Choi et al.

(10) Patent No.: US 9,807,526 B2
(45) Date of Patent: Oct. 31, 2017

(54) APPARATUS AND METHOD FOR DETERMINING PARAMETER USING AUDITORY MODEL OF HEARING LOSS PATIENT

(71) Applicant: SAMSUNG ELECTRONICS CO., LTD., Suwon-si (KR)

(72) Inventors: Jong Min Choi, Seoul (KR); Yun Seo Ku, Seoul (KR); Dong Wook Kim, Seoul (KR); Jong Jin Kim, Hwaseong-si (KR); Jun Il Sohn, Yongin-si (KR); Jun Whon Uhm, Anyang-si (KR); Jong Hee Han, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 269 days.

(21) Appl. No.: 14/226,118

(22) Filed: Mar. 26, 2014

(65) Prior Publication Data

US 2014/0294187 A1   Oct. 2, 2014

(30) Foreign Application Priority Data

Apr. 2, 2013 (KR) .................. 10-2013-0036018

(51) Int. Cl.
*H04R 25/00* (2006.01)
*A61B 5/12* (2006.01)
*A61B 5/0484* (2006.01)

(52) U.S. Cl.
CPC ............ *H04R 25/70* (2013.01); *A61B 5/125* (2013.01); *A61B 5/04845* (2013.01); *H04R 25/305* (2013.01); *H04R 2430/03* (2013.01); *H04R 2460/03* (2013.01)

(58) Field of Classification Search
None
See application file for complete search history.

(56) References Cited

U.S. PATENT DOCUMENTS 4,366,349 A   12/1982 Adelman
4,953,112 A   8/1990 Widin et al.
(Continued)

FOREIGN PATENT DOCUMENTS

JP   2002-369292 A   12/2002
JP   2003-264892 A   9/2003
(Continued)

OTHER PUBLICATIONS

European Examination Report issued by the European Patent Office on Sep. 19, 2014 in counterpart European Application No. 13192991.1. (8 pages, in English).
(Continued)

*Primary Examiner* — Curtis Kuntz
*Assistant Examiner* — Kenny Truong
(74) *Attorney, Agent, or Firm* — NSIP Law

(57) ABSTRACT

An apparatus and method are provided to determine a parameter using an auditory model of a hearing loss patient. The parameter determination apparatus determines a similarity between a neurogram of a normal subject and a neurogram of a hearing loss patient, and determines an optimal frequency band for the hearing loss patient based on the similarity.

15 Claims, 6 Drawing Sheets

(56) References Cited

U.S. PATENT DOCUMENTS

| | | | |
|---|---|---|---|
| 2004/0028250 A1* | 2/2004 | Shim | H04R 25/70 |
| | | | 381/312 |
| 2006/0023907 A1 | 2/2006 | Kasztelan | |
| 2006/0159285 A1 | 7/2006 | Reber et al. | |
| 2006/0222193 A1 | 10/2006 | Tohyama et al. | |
| 2011/0033073 A1 | 2/2011 | Inoshita et al. | |
| 2011/0200216 A1 | 8/2011 | Lee et al. | |
| 2012/0243715 A1* | 9/2012 | Pedersen | H04R 25/505 |
| | | | 381/316 |
| 2014/0294188 A1* | 10/2014 | Rini | H04R 25/70 |
| | | | 381/60 |

FOREIGN PATENT DOCUMENTS

| | | |
|---|---|---|
| JP | 2008-042787 A | 2/2008 |
| KR | 1998-021549 A | 6/1998 |
| KR | 2001-0001863 A | 1/2001 |
| KR | 10-2004-0019147 A | 3/2004 |
| KR | 10-2005-0019686 A | 3/2005 |
| KR | 10-2005-0092133 A | 9/2005 |
| KR | 10-2010-0042370 A | 4/2010 |
| KR | 10-0974153 B1 | 8/2010 |
| WO | WO 01/78449 A1 | 10/2001 |

OTHER PUBLICATIONS

Leung, B. "Physiological Assessment of Hearing Aid Compression Schemes." Department of Electrical and Biomedical Engineering, McMaster University, Aug. 2008 (64 pages, in English).

European Extended Search Report issued by the European Patent Office on Mar. 21, 2014 corresponding to European Patent Application No. 13192991.1 (10 pages).

Yund, E. William, et al., "Multichannel compression hearing aids: Effect of number of channels on speech discrimination in noise." The Journal of the Acoustical Society of America 97.2 (1995): 1206-1223.

Dinath, Faheem, et al. "Hearing aid gain prescriptions balance restoration of auditory nerve mean-rate and spike-timing representations of speech." 30th Annual International IEEE EMBS Conference (2008). 1793-1796.

\* cited by examiner

APPARATUS AND METHOD FOR DETERMINING PARAMETER USING AUDITORY MODEL OF HEARING LOSS PATIENT

CROSS-REFERENCE TO RELATED APPLICATION(S)

This application claims the benefit under 35 USC §119(a) of Korean Patent Application No. 10-2013-0036018, filed on Apr. 2, 2013, in the Korean Intellectual Property Office, the entire disclosure of which is incorporated herein by reference for all purposes.

BACKGROUND

1. Field

The following description relates to an apparatus and method to determine a parameter, and more particularly, to an apparatus and method to determine an optimal frequency band for a hearing loss patient using an auditory model.

2. Description of Related Art

A hearing aid, which is a hearing device for a hearing loss patient, conventionally has a multi-frequency band. A frequency band of the hearing device is preset to 4 channels, 8 channels, 16 channels, and the like.

The frequency band can be adjusted through software provided outside or inside the hearing device. Conventionally, frequency bands of hearing devices of hearing loss patients are statistically collected, and an optimal frequency band for a particular hearing loss patient is determined using the collected frequency bands. Such a statistical method to determine the frequency band may not be appropriate for a hearing aid of a particular hearing loss patient who may have hearing loss diagnostics different from other patients.

When the frequency band is increased, hearing loss compensation increases. However, when the frequency band is excessively high, an amount of calculation to compensate for hearing loss would be excessive thereby reducing an operating efficiency of the hearing device. Furthermore, power consumption of the hearing device would increase. In contrast, when the frequency band is insufficient, a compensation effect for the hearing loss of a patient may be unsatisfactory.

Accordingly, there is a demand for a method to determine an optimal frequency band for a hearing device of a particular patient.

SUMMARY

In an aspect, there is provided a parameter determination apparatus including a similarity determiner configured to determine similarity between a neurogram of a normal person and a neurogram of a hearing loss patient, and a frequency band determiner configured to determine an optimal frequency band for the hearing loss patient based on the similarity.

In accordance with an illustrative example, a parameter determination apparatus, includes a similarity determiner configured to determine a similarity between a reference neurogram and a patient neurogram; and a frequency band determiner configured to determine an optimal frequency band based on the similarity.

The frequency band determiner is configured to determine the optimal frequency band based on a change tendency of the similarity output according to an increase of a frequency band.

The patient neurogram is determined according to an auditory model of the hearing loss patient.

The auditory model of the hearing loss patient is determined based on at least one of a damage degree of a middle ear, a damage degree of an inner hair cell, and an outer hair cell of an inner ear.

The patient neurogram is output when sound applying hearing loss compensation is applied to an auditory model of the hearing loss patient.

The optimal frequency band is a calibrating parameter to control a hearing device of the hearing loss patient.

The optimal frequency band determiner is configured to determine the optimal frequency band based on a threshold of the similarity or a gradient of the similarity with respect to the frequency band.

The frequency band determiner wired or wirelessly transmits the optimal frequency band to optimize and reduce power consumption of the device.

The patient neurogram is varied according to an auditory model of a patient and the reference neurogram is a neurogram of a normal person.

The frequency band determiner considers a tendency and a change of the reference neurogram and the patient neurogram with the increase of a frequency band.

In accordance with another illustrative example, there is provided an apparatus, including a hearing device configured to receive an optimal frequency band for a hearing loss patient and automatically calibrate the hearing device to adapt to the hearing loss patient, wherein the optimal frequency band for the hearing loss patient is based on an auditory model of the hearing loss patient.

The optimal frequency band for the hearing loss patient is determined using a similarity between a reference neurogram and a patient neurogram.

The patient neurogram is determined based on a change tendency of the similarity output according to an increase of a frequency band.

In accordance with an illustrative example, there is provided a parameter determination method including determining a similarity between a reference neurogram and a patient neurogram; and determining an optimal frequency band based on the similarity.

The determining of the optimal frequency band includes determining the optimal frequency band based on a change tendency of the similarity output according to an increase of a frequency band.

The method also includes determining the neurogram of the hearing loss patient according to an auditory model of the hearing loss patient.

The method includes determining the auditory model of the hearing loss patient based on at least one of a damage degree of a middle ear, a damage degree of an inner hair cell, and an outer hair cell of an inner ear.

The method includes outputting the neurogram of the hearing loss patient when sound applying hearing loss compensation is applied to an auditory model of the hearing loss patient.

The optimal frequency band is a calibrating parameter to control a hearing device of the hearing loss patient.

The determining of the optimal frequency band includes determining the optimal frequency band considering a threshold of the similarity and a gradient of the similarity with respect to the frequency band.

Other features and aspects will be apparent from the following detailed description, the drawings, and the claims.

Figure 1:
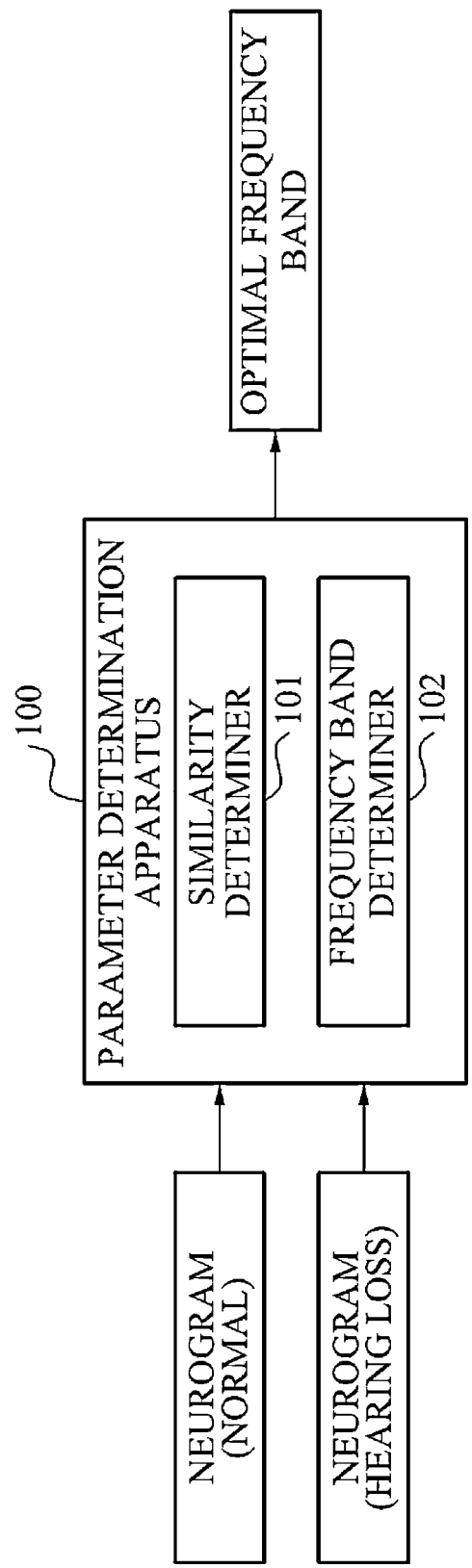
FIG. 1 is a diagram illustrating an example of a parameter determination apparatus, in accordance with an illustrative example.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses, and/or methods described herein will be suggested to those of ordinary skill in the art. The progression of processing steps and/or operations described is an example; however, the sequence of steps and/or operations is not limited to that set forth herein and may be changed as is known in the art, with the exception of steps and/or operations necessarily occurring in a certain order. Also, description of well-known functions and constructions may be omitted for increased clarity and conciseness.

An optimal frequency band output of a parameter determination apparatus, according to an embodiment, may be used to calibrate a hearing device for a hearing loss patient. In one example, the optimal frequency band is determined in accordance with an auditory model of a hearing loss patient wearing the hearing device. The auditory model reflects a hearing loss parameter of the hearing loss patient.

The auditory model refers to a modeling result of an outer ear, a middle ear, and an inner ear. Parameters may be set in the auditory model according to hearing loss information of the hearing loss patient. For example, the hearing loss information may include a damage degree of the middle ear, a damage degree of an inner hair cell, and/or an outer hair cell in the inner ear.

When external sound stimulation is transmitted to the auditory model, the auditory model may result in neural spikes of an auditory nerve fiber or may cause the auditory nerve fiber to generate neural spikes. The neural spikes may be expressed as a neurogram of an auditory nerve similar to a spectrogram of the sound stimulation.

FIG. 1 illustrates an example of a parameter determination apparatus 100, in accord with an illustrative example.

Referring to FIG. 1, the parameter determination apparatus 100 may include a similarity determiner 101 and a frequency band determiner 102.

The similarity determiner 101 may determine a similarity between a neurogram of a normal person or any living subject and a neurogram of a hearing loss patient or hearing loss subject. The neurogram of a normal person or a normal living subject may be a neurogram used as a reference neurogram. The normal person or the living subject is a person or animal with unimpaired hearing. The neurogram of the hearing loss patient may be varied according to an auditory model of the hearing loss patient. The neurogram refers to an output of the auditory model with respect to an external sound stimulation. The auditory model of the hearing loss patient may be determined by a damage degree of a middle ear, a damage degree of an inner hair cell, and/or an outer hair cell of an inner ear.

For example, once a sound applied to a hearing loss compensation algorithm is provided to a hearing loss patient, the similarity determiner 101 may compare a normal hearing neurogram, which is an output of the auditory model of a normal person, with an aided neurogram, which is an output of the auditory model of the hearing loss patient. A similarity between the normal hearing neurogram and the aided neurogram may be expressed by an index.

The frequency band determiner 102 may determine an optimal frequency band with respect to the hearing loss patient based on the similarity or the index. For example, the frequency band determiner 102 may determine the optimal frequency band by considering a tendency, a change, and/or a similarity between the normal hearing neurogram and the aided neurogram with an increase of the frequency band.

The frequency band determiner 102 may determine the optimal frequency band by considering a threshold of the similarity or a gradient of the similarity with respect to the frequency band. In one illustrative example, the optimal frequency band refers to a calibration parameter or parameter that enables the hearing device to operate most efficiently and optimally to control the hearing device of the hearing loss patient.

As the frequency band increases, the sound may be analyzed in further detail and, therefore, a hearing loss compensation effect may be increased. However, the hearing loss compensation effect does not increase in proportion with the frequency band being continuously increased. Furthermore, increase in the frequency band may increase power consumption of the hearing device. Therefore, once the optimal frequency band with respect to the hearing loss patient is determined, the hearing loss compensation effect may be increased while power consumption of the hearing device is reduced.

The optimal frequency band output from the parameter determination apparatus 100 may be used to calibrate the hearing device and minimize power consumption and maximize output of the hearing device of the hearing loss patient. When data related to the optimal frequency band for the hearing loss patient is transmitted wired or wirelessly from the frequency band determiner 102 of the parameter determination apparatus 100, the hearing device may be optimized according to the data.

Figure 2:
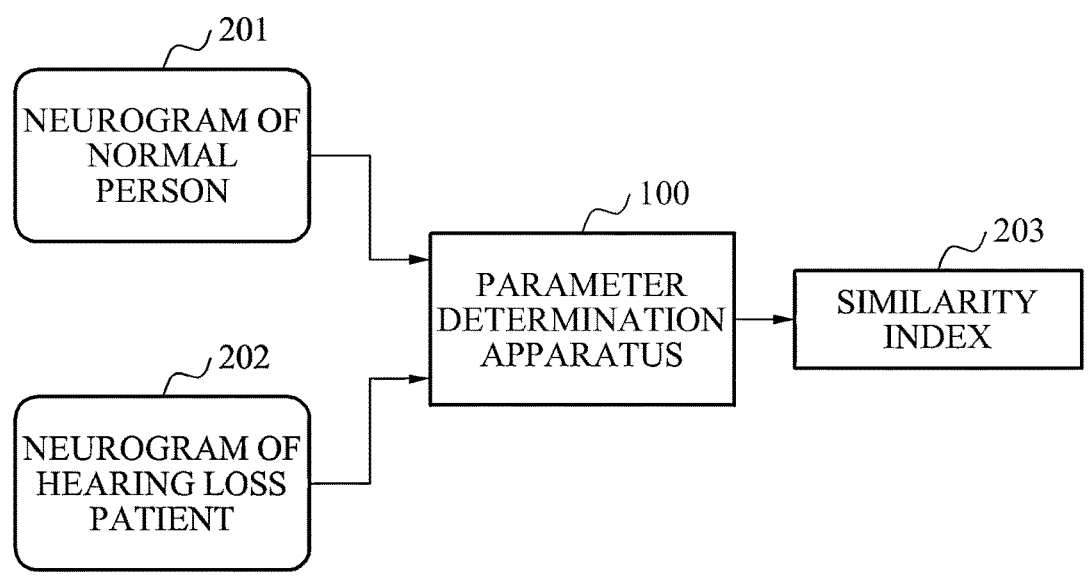
FIG. 2 is a diagram illustrating an example process comparing a neurogram of a hearing loss patient and a neurogram of a normal person, in accordance with an illustrative example.

FIG. 2 illustrates an example process of comparing a neurogram 202 of a hearing loss patient and a neurogram 201 of a normal person, in accordance with an illustrative example.

Referring to FIG. 2, the parameter determination apparatus 100 may extract a similarity index 203 by comparing the neurogram 201 of the normal person and the neurogram 202 of the hearing loss patient. In one illustrative example, the parameter determination apparatus 100 may repeat extraction of the similarity index 203 while increasing the frequency band. As previously explained, the neurogram 202 of the hearing loss patient refers to the output of the auditory model of the hearing loss patient when the sound stimulation applying the hearing loss compensation algorithm is provided to the hearing loss patient.

Figure 3:
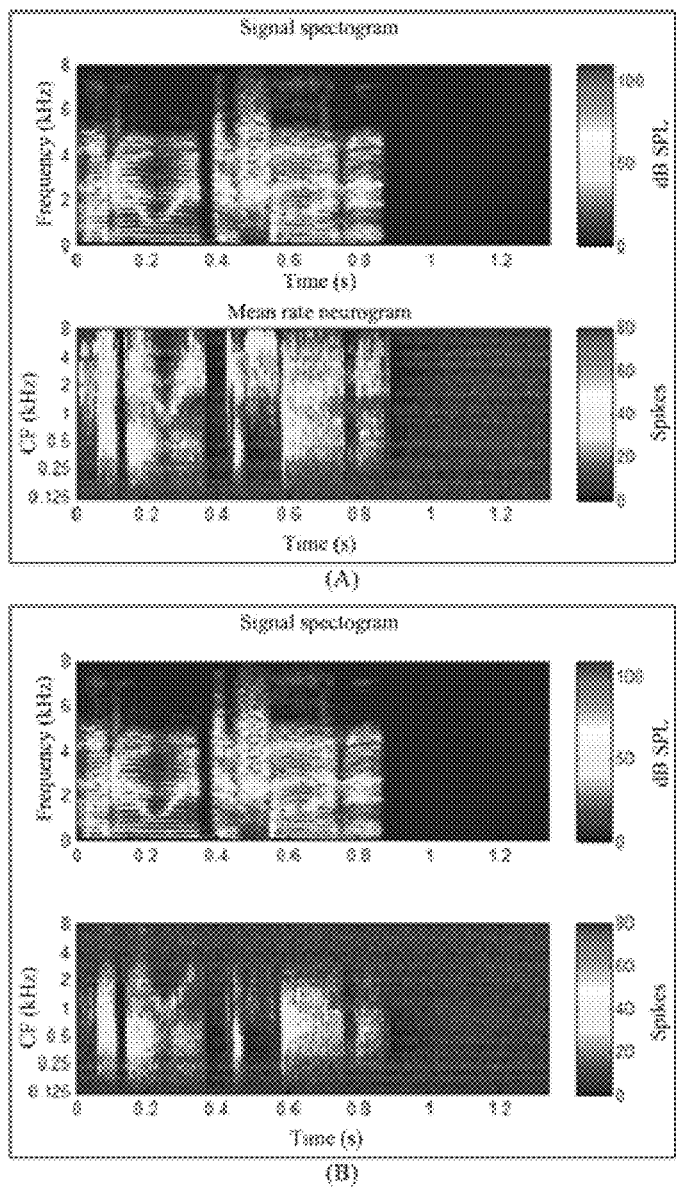
FIG. 3 is a diagram illustrating an example of neurograms of a hearing loss patient and a normal person with respect to a sound stimulation, in accordance with an illustrative example.

FIG. 3 illustrates an example of neurograms of a hearing loss patient and a normal person with respect to a sound stimulation, in accordance with an illustrative example.

Case (A) shows the neurogram of the normal person with respect to an external sound stimulation. Case (B) shows the neurogram of the hearing loss patient with respect to the external sound stimulation. In Case (B), the sound stimulation not applying a hearing loss compensation algorithm is transmitted to the hearing loss patient.

Figure 4:
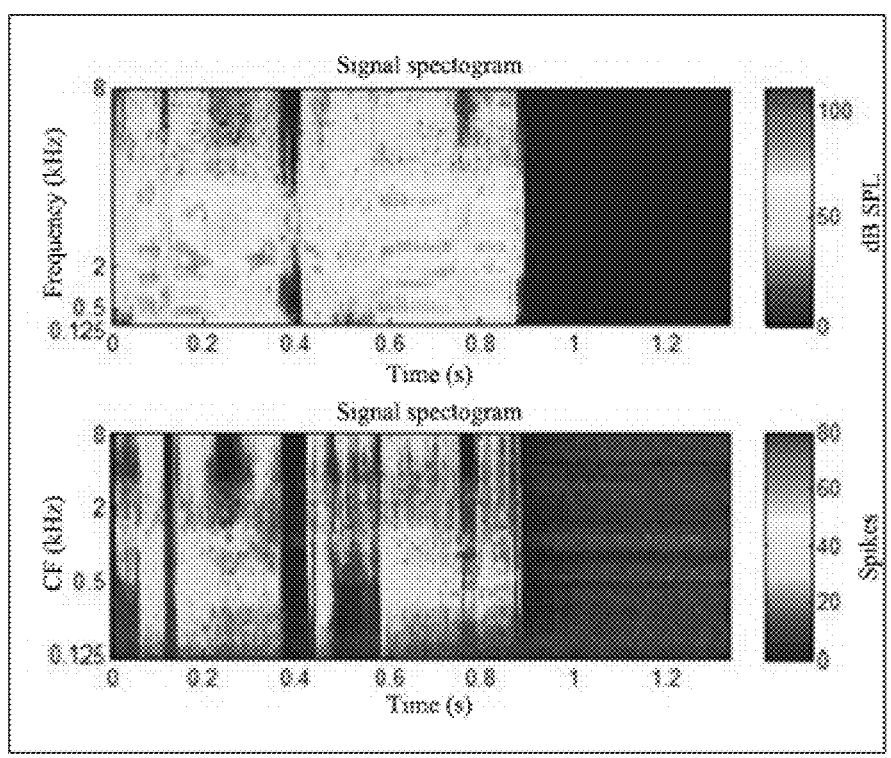
FIG. 4 is a diagram illustrating an example of a neurogram of a hearing loss patient with respect to a sound stimulation compensating for hearing loss, in accordance with an illustrative example.

FIG. 4 illustrates an example of a neurogram of a hearing loss patient with respect to a sound stimulation compensating for hearing loss, in accordance with an illustrative configuration.

The neurogram of the hearing loss patient may be used to determine the optimal frequency band for the hearing loss patient using the hearing loss information. In one example, the neurogram of the hearing loss patient may refer to a neurogram output when a sound stimulation applied to the hearing loss compensation algorithm is input to the auditory model.

The parameter determination apparatus 100 may compare a normal hearing neurogram, which is the output of the auditory model of the normal person, with the aided neurogram, which is the output of the auditory model of the hearing loss patient, when the sound stimulation applied to the hearing loss compensation algorithm is provided to the hearing loss patient. A similarity between the normal hearing neurogram and the aided neurogram may be expressed by an index.

The parameter determination apparatus 100 may determine the optimal frequency band for the hearing loss patient by analyzing a change tendency of the similarity expressed by the index while increasing the frequency band. The determined optimal frequency band is used to calibrate the hearing device to minimize power consumption and maximize output of the hearing device of the hearing loss patient.

Figure 5:
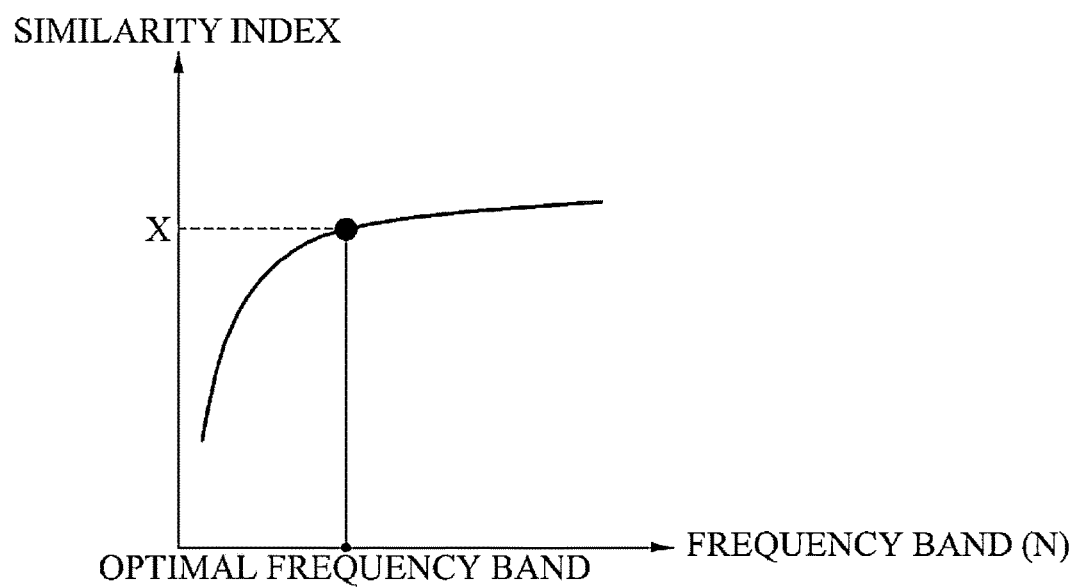
FIG. 5 is a diagram illustrating an example of relations between a frequency band and a similarity index, in accordance with an illustrative example.

FIG. 5 illustrates an example of relations between a frequency band and a similarity index, in accordance with an illustrative example.

Referring to FIG. 5, a similarity index increases according to an increase of the frequency band. As aforementioned, the similarity index refers to the similarity between the normal hearing neurogram, which is the output of the auditory model of the normal person, and the aided neurogram, which is the output of the auditory model of the hearing loss patient when the sound stimulation applied to the hearing loss compensation algorithm is provided to the hearing loss patient.

As the frequency band increases, the hearing device divides an input sound. Accordingly, the hearing loss compensation effect may be increased. However, because the increase in the frequency band influences power consumption of the hearing device, the frequency band is impractical to be continuously increased. Furthermore, when the frequency band increases to a certain level, the hearing loss compensation effect tapers or does not increase in a linear proportion to the frequency band.

To minimize power consumption of the hearing device and improve the hearing loss compensation effect, the parameter determination apparatus 100 may determine the optimal frequency band by considering the change tendency of the similarity index according to the increase of the frequency band. For example, the parameter determination apparatus 100 may determine the optimal frequency band by considering whether the similarity index exceeds a predetermined threshold index. Alternatively, the similarity 100 may consider whether a gradient of the similarity index according to the frequency band is less than or equal to a predetermined threshold gradient. As illustrated in FIG. 5, in one example, a frequency band of when the similarity index is X may be determined as the optimal frequency band.

Figure 6:
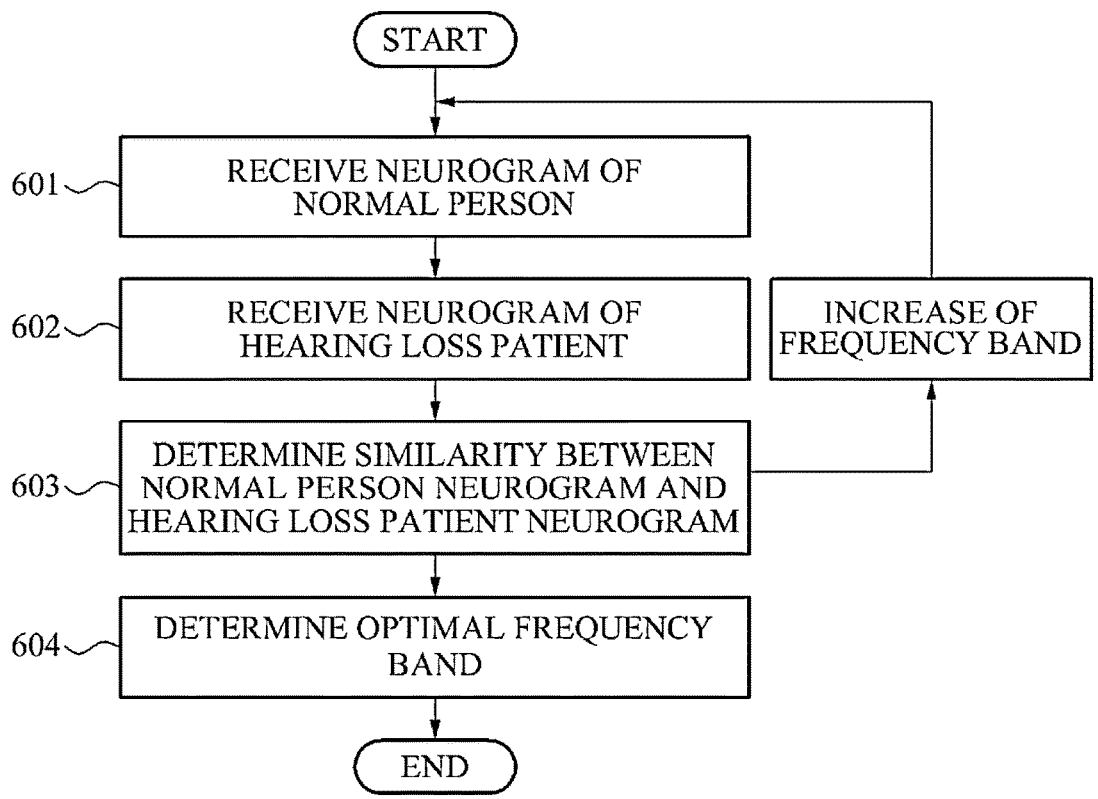
FIG. 6 is a diagram illustrating an example of a parameter determination method, in accordance with an illustrative example.

FIG. 6 illustrates an example of a parameter determination method, in accordance with an illustrative example.

In operation 601, the method performed at the parameter determination apparatus 100 may receive the neurogram of the normal person. The neurogram of the normal person refers to the neurogram output from the auditory model of the normal person.

In operation 602, the method performed at the parameter determination apparatus 100 may receive the neurogram of the hearing loss patient. The neurogram of the hearing loss patient refers to the neurogram output from the auditory model of the hearing loss patient.

In operation 603, the method performed at the parameter determination apparatus 100 may determine a similarity between the normal hearing neurogram and the aided neurogram. The similarity may be expressed by an index. Operations 601, 602, and 603 may be repeatedly performed as the frequency band is increased.

In operation 604, the method performed at the parameter determination apparatus 100 may determine the optimal frequency band for the hearing loss patient. For example, the method may determine the optimal frequency band for the hearing loss patient considering the change tendency of the similarity or similarity index output according to the increase of the frequency band. In one example, the method may determine the optimal frequency band by considering a threshold of the similarity or a gradient of the similarity with respect to the frequency band.

The method performed at the parameter determination apparatus 100 may determine the optimal frequency band using an auditory model reflecting hearing loss information of the hearing loss patient. In detail, the parameter determination apparatus 100 may determine the similarity between the neurogram output from the auditory model of the normal person and the neurogram output, through the sound stimulation in which hearing loss is compensated, from the auditory model of the hearing loss patient.

The similarity determination may be repeatedly performed while the frequency band is increased. The method performed at the parameter determination apparatus 100 may determine the optimal frequency band for the hearing loss patient in consideration of the change tendency of the similarity according to an increase in the frequency band. The frequency band may be used to calibrate the hearing device of the hearing loss patient.

According to an embodiment, hearing loss information of the hearing loss patient may be received and processed more accurately by determining the frequency band using the neurogram, which is the output of the auditory model. In addition, because the optimal frequency band is determined in consideration of the change tendency of the similarity according to the increase in the frequency band, power consumption of the hearing device may be minimized The parameter determination apparatus 100, according to an embodiment, may include a similarity determiner 101 to determine a similarity or an index between a reference neurogram and a patient neurogram, and a frequency band determiner 102 to determine the optimal frequency band in consideration of the similarity or the index.

The frequency band determiner 102 may determine the optimal frequency band based on the change tendency of the similarity output according to an increase in the frequency band.

In one configuration, the patient neurogram is determined according to an auditory model of the hearing loss patient. The auditory model of the hearing loss patient may be determined based on at least one of the damage degree of the middle ear, the damage degree of the inner hair cell, and the outer hair cell of the inner ear, and the like.

In one example, the patient neurogram is the neurogram output when the sound applying hearing loss compensation is applied to the auditory model of a hearing loss patient. The optimal frequency band is a calibration parameter to control a hearing device of the hearing loss patient.

The optimal frequency band determiner 102 may determine the optimal frequency band by considering the threshold of the similarity or the index or the gradient of the similarity or the index with respect to the hearing loss patient. In one illustrative example, the hearing device may receive an optimal frequency band and automatically, without user intervention, calibrates the hearing device to adapt to the hearing loss patient. The optimal frequency band is based on an auditory model of the hearing loss patient.

The parameter determination apparatus 100 may determine the optimal frequency band using the similarity or the index between the neurogram of the normal subject and the neurogram of the hearing loss patient. The parameter determination apparatus 100 also may determine the optimal frequency band by considering the change tendency of the similarity or the index output according to the increase of the frequency band.

The parameter determination method, according to an embodiment, may include determining similarity or index between the reference neurogram and the patient neurogram, and determining the optimal frequency band by considering the similarity.

In one configuration, the determining of the optimal frequency band may determine the optimal frequency band by considering the change tendency of the similarity output according to the increase in the frequency band. The patient neurogram may be determined differently according to the auditory model of the hearing loss patient.

In one illustrative example, the auditory model of the hearing loss patient is determined by at least one of the damage degree of the middle ear, the damage degree of the inner hair cell, and the outer hair cell of the inner ear, and the like. The patient neurogram may be the neurogram output when the sound applying hearing loss compensation is applied to the auditory model of the hearing loss patient. The optimal frequency band is a calibrating parameter to control the hearing device of the hearing loss patient. The determining of the optimal frequency band may determine the optimal frequency band by considering the threshold of the similarity or the index or the gradient of the similarity or the index with respect to the hearing loss patient.

A method of calibrating a hearing device, according to an embodiment, may include receiving an optimal frequency band for a hearing loss patient from a parameter determination apparatus 100 and automatically calibrating the optimal frequency band corresponding to the hearing loss patient.

In one illustrative example, the parameter determination apparatus 100 may determine the optimal frequency band for the hearing loss patient using an auditory model of the hearing loss patient. The parameter determination apparatus 100 may determine the optimal frequency band for the hearing loss patient using the similarity or the index between the neurogram of the normal subject and the neurogram of the hearing loss patient. The parameter determination apparatus 100 may determine the optimal frequency band by considering the change tendency of the similarity or the index output according to the increase in the frequency band.

The parameter determination apparatus 100, the similarity determiner 101, and the frequency band determiner 102 described herein may be implemented using hardware components. The hardware components may include, for example, controllers, processors, generators, drivers, and other equivalent electronic components. The hardware components may be implemented using one or more general-purpose or special purpose computers, such as, for example, a processor, a controller, an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The above-described embodiments may be recorded, stored, or fixed in one or more non-transitory computer-readable media that may include program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A parameter determination apparatus, comprising:
a processor configured to determine a similarity index between a reference neurogram and a patient neurogram; and
a frequency band determiner configured to determine an optimal frequency band based on the similarity index between a reference neurogram and a patient neurogram,
wherein the optimal frequency band is based on a rate of change of the similarity index as a function of the frequency band, and the optimal frequency band is used to calibrate a hearing device for a hearing loss patient.

2. The parameter determination apparatus of claim 1, wherein the patient neurogram is determined according to an auditory model of the hearing loss patient.

3. The parameter determination apparatus of claim 2, wherein the auditory model of the hearing loss patient is determined based on at least one of a damage degree of a middle ear, a damage degree of an inner hair cell, and an outer hair cell of an inner ear.

4. The parameter determination apparatus of claim 1, wherein the patient neurogram is output when sound applying hearing loss compensation is applied to an auditory model of the hearing loss patient.

5. The parameter determination apparatus of claim 1, wherein the optimal frequency band is a calibrating parameter to control the hearing device of the hearing loss patient.

6. The parameter determination apparatus of claim 1, wherein the frequency band determiner is configured to determine the optimal frequency band based on whether the similarity index exceeds a threshold value or whether a gradient of the similarity index is less than or equal to a threshold gradient.

7. The parameter determination apparatus of claim 1, wherein the frequency band determiner wired or wirelessly transmits the optimal frequency band to optimize and reduce power consumption of the hearing device.

8. The parameter determination apparatus of claim 1, wherein the patient neurogram is varied according to an auditory model of a patient and the reference neurogram is a neurogram of a normal person.

9. An apparatus, comprising:
a hearing device configured to receive an optimal frequency band for a hearing loss patient and automatically calibrate the hearing device to adapt to the hearing loss patient, wherein the optimal frequency band is based on an auditory model of the hearing loss patient and based on a similarity index between a reference neurogram and a patient neurogram of the hearing loss patient,
wherein the optimal frequency band is based on a rate of change of the similarity index as a function of the frequency band.

10. A parameter determination method, comprising:
determining a similarity index between a reference neurogram and a patient neurogram;
determining an optimal frequency band between a reference neurogram and a patient neurogram based on the similarity index of the patient neurogram with respect to the reference neurogram; and
applying the optimal frequency band to calibrate a hearing device for a hearing loss patient,
wherein the determining of the optimal frequency band comprises determining an optimal frequency band based on a rate of change of the similarity index as a function of the frequency band.

11. The parameter determination method of claim 10, further comprising:
determining the neurogram of the hearing loss patient according to an auditory model of the hearing loss patient.

12. The parameter determination method of claim 11, further comprising:
determining the auditory model of the hearing loss patient based on at least one of a damage degree of a middle ear, a damage degree of an inner hair cell, and an outer hair cell of an inner ear.

13. The parameter determination method of claim 10, further comprising:
outputting the neurogram of the hearing loss patient when sound applying hearing loss compensation is applied to an auditory model of the hearing loss patient.

14. The parameter determination method of claim 10, wherein the optimal frequency band is a calibrating parameter to control the hearing device of the hearing loss patient.

15. The parameter determination method of claim 10, wherein the determining of the optimal frequency band comprises
determining an optimal frequency band considering whether a threshold value related to the similarity index or a gradient of the similarity index changed according to the frequency band being less than or equal to a threshold gradient.

* * * * *